(12) United States Patent
Furukawa

(10) Patent No.: US 10,688,245 B2
(45) Date of Patent: Jun. 23, 2020

(54) PLUNGER FOR SYRINGE AND PRE-FILLED SYRINGE INCLUDING THE SAME

(71) Applicant: TERUMO KABUSHIKI KAISHA, Tokyo (JP)

(72) Inventor: Koichiro Furukawa, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 66 days.

(21) Appl. No.: 15/923,981

(22) Filed: Mar. 16, 2018

(65) Prior Publication Data

US 2018/0200447 A1    Jul. 19, 2018

Related U.S. Application Data

(63) Continuation of application No. PCT/JP2016/073560, filed on Aug. 10, 2016.

(30) Foreign Application Priority Data

Sep. 17, 2015   (JP) .................................. 2015-184176

(51) Int. Cl.
*A61M 5/315* (2006.01)
*A61M 5/28* (2006.01)
*A61M 5/00* (2006.01)

(52) U.S. Cl.
CPC .......... *A61M 5/31501* (2013.01); *A61M 5/28* (2013.01); *A61M 5/31513* (2013.01);
(Continued)

(58) Field of Classification Search
CPC .......... A61M 5/31501; A61M 5/31513; A61M 5/28; A61M 2005/31508;
(Continued)

(56) References Cited

U.S. PATENT DOCUMENTS 7,824,380 B2 * 11/2010 Iijima ................ A61M 5/31511
                                                  604/218
2004/0030345 A1 * 2/2004 Aurin ................. A61B 17/8816
                                                  606/92
(Continued)

FOREIGN PATENT DOCUMENTS

JP   2006-272009 A   10/2006
JP   2011-115446 A   6/2011
(Continued)

OTHER PUBLICATIONS

International Search Report with English language translation and Written Opinion dated Nov. 8, 2016 in International Application No. PCT/JP2016/073560.

*Primary Examiner* — Kami A Bosworth
*Assistant Examiner* — Antarius S Daniel
(74) *Attorney, Agent, or Firm* — Foley & Lardner LLP

(57) ABSTRACT

A plunger for a syringe that includes a barrel includes: a gasket mounting portion located at a distal end of the plunger; a disk positioned at a proximal end of the gasket mounting portion; a shaft extending proximally from the disk, wherein the shaft comprises a plurality of slats extending proximally from the disk; a pressing portion located at a lower end of the shaft; and a plunger inclination-prevention unit that is located at a distal end of the shaft and is configured to inhibit the plunger from inclining inside the barrel of the syringe. The plunger inclination-prevention unit comprises one or more axially inclined plates, each having a first end disposed on the disk, extending obliquely proximal with respect to a central axis of the shaft, and having a second end disposed on one of the slats.

8 Claims, 18 Drawing Sheets

(52) U.S. Cl.
CPC ... *A61M 5/007* (2013.01); *A61M 2005/31508* (2013.01); *A61M 2005/31521* (2013.01)

(58) Field of Classification Search
CPC ........ A61M 2005/31521; A61M 5/007; A61M 2005/3101; A61M 5/31511; A61M 2005/3151
See application file for complete search history.

(56) References Cited

U.S. PATENT DOCUMENTS

| | | |
|---|---|---|
| 2008/0051728 A1 | 2/2008 | Iijima et al. |
| 2010/0057014 A1 | 3/2010 | Cane |
| 2013/0116628 A1* | 5/2013 | Kulshrestha ....... A61M 5/31511 604/227 |

FOREIGN PATENT DOCUMENTS

| | | |
|---|---|---|
| JP | 2014-087502 A | 5/2014 |
| WO | WO-01/05456 A1 | 1/2001 |

* cited by examiner

PLUNGER FOR SYRINGE AND PRE-FILLED SYRINGE INCLUDING THE SAME

CROSS-REFERENCE TO RELATED APPLICATIONS

The present application claims priority to PCT Application No. PCT/JP2016/073560, filed on Aug. 10, 2016, which claims priority to Japanese application number 2015-184176 filed on Sep. 17, 2015. The contents of these applications are hereby incorporated by reference in their entireties.

BACKGROUND

The present disclosure relates to a plunger for a syringe and a pre-filled syringe including the plunger.

In recent years, a pre-filled syringe that is pre-filled with a medicinal solution has been widely used.

Examples of the pre-filled syringe include those with a plunger not pre-mounted on a gasket and to be mounted on the gasket in use, and those with a plunger that is pre-mounted on a gasket.

A pre-filled syringe with a plunger that is mounted on a gasket is manufactured by what is called a vacuum capper method. In the vacuum capper method, a drug (pharmaceutical) is filled inside a barrel that has an opening sealed at a leading end, and the gasket is placed at the opening of the barrel in an atmosphere under reduced pressure (atmosphere under vacuum), and then, the plunger is inserted into the barrel under ordinary pressure, thereby mounting the plunger on the gasket. Preliminarily mounting the plunger makes it difficult to dispose the gasket in the opening of the barrel, so that the aforementioned capping operation is performed with the gasket alone. For this reason, it is common that a subsequent plunger mounting operation is required in a pre-filled syringe. In regard to a pre-filled syringe with a plunger that is not pre-mounted on a gasket, a user performs the operation of mounting the plunger on the gasket in use.

In a typical pre-filled syringe, an external thread and an internal thread are provided in a plunger and a gasket, respectively, and both threads are screwed together so as to form a mounting mechanism.

An example of a pre-filled syringe is disclosed in WO 01/005456 (US 2008-0051728-A1).

WO 01/005456 discloses a plunger for a syringe in which a gasket can be attached to a thread disposed in a leading end of the plunger, while a central axis of a syringe barrel and a central axis of the plunger are simply aligned. The plunger of WO 01/005456 has the leading end formed with a thread 10 to which a gasket 25 provided in a syringe 2 is attached. A pair of ring members 12 and 13 are arranged at an interval at the back (right side in FIG. 1) of the thread 10, and a plurality of wing members 14 are disposed between the ring members 12 and 13. One ring member 12 is disposed in contact with the thread 10 at the leading end of the plunger 1, and the other ring member 13 is apart in the rearward of the ring member 12. The interval between the ring members 12 and 13 is 0.5 mm or more.

In addition, the present applicant has proposed a configuration in JP 2014-87502 A. A plunger 5 disclosed in JP 2014-87502 A is provided with four reinforcement units 54 provided at a leading end of a body section 50. As illustrated in FIGS. 17 to 19, each reinforcement unit 54 includes a plate-like axial reinforcement unit 54a and a circumferential reinforcement unit 54b having a first end jointed with the axial reinforcement unit 54a. The axial reinforcement unit 54a is formed in a slat-like shape extending by a predetermined length perpendicularly from a surface of any one of slats 51a, 51b, 51c, and 51d included in a shaft and perpendicularly from a rear end surface of a flange 56. The axial reinforcement unit 54a is substantially parallel to a central axis of the plunger. It is preferable that the axial reinforcement unit 54a has a one-sixth or one-quarter axial length of the entire length of the shaft (the entire length of the slat). Furthermore, as illustrated in FIG. 18, the axial reinforcement unit 54a has a terminal end (base end) that is chamfered or arched.

The circumferential reinforcement unit 54b is provided at a position slightly closer to the leading end (closer to the flange 56) than to the base end of the axial reinforcement unit. The circumferential reinforcement unit connects the axial reinforcement unit 54a with the opposing shaft and has a first end in a circumferential direction extending from one side surface of the axial reinforcement unit 54a, and a second end reaching the slat that opposes the axial reinforcement unit 54a. The circumferential reinforcement unit also has a bottom surface connected to the slat from which the axial reinforcement unit 54a protrudes. In other words, the circumferential reinforcement unit 54b connects two slats with the axial reinforcement unit 54a adjacent to the circumferential reinforcement unit 54b. In addition, the circumferential reinforcement unit 54b is substantially parallel to the flange 56.

The aforementioned pre-filled syringe is not a limited example of a syringe, and it is often the case that the air inside of a syringe is required to be removed when the syringe is used. In a case in which a syringe is filled with a liquid having high viscosity or in a case in which a large syringe having a large amount of liquid filled is used, it is necessary to apply a large load during this air vent operation. During this air vent operation, particularly, at the time of initially moving a plunger, the plunger tends to incline because of a small portion that enters a barrel, and such inclination may lead to liquid leakage. A syringe filled with a liquid is often used while mounted on a syringe pump. Even in use of this syringe pump, at the time of initially moving a plunger, the plunger tends to incline because of a small portion that enters a barrel, and such inclination may lead to liquid leakage.

SUMMARY

In the plunger disclosed in WO 01/005456, the pair of ring members 12 and 13 are arranged at an interval, and the plurality of wing members 14 are disposed between the ring members 12 and 13, so that inclination of the plunger inside the barrel can be prevented to some extent. However, the wing members 14 provided between the pair of ring members 12 and 13 extend parallel to an axial direction of the plunger, and there is a portion with no wing member between the wing members 14. When the plunger inclines, in a case in which the wing members abut against an inner surface of the barrel, the inclination is prevented, but in a case in which the plunger inclines toward the portion with no wing member, the inclination of the plunger cannot be prevented sufficiently. Furthermore, the portion with no wing member is considerably larger than portions with wing member. Therefore, in this plunger, as a whole, the inclination of the plunger inside the barrel is prevented insufficiently.

Similarly, even in the plunger disclosed in JP 2014-87502 A, such reinforcement units are capable of inhibiting, to some extent, the plunger mounted on the gasket from inclining inside the barrel, but there is a portion with no reinforcement unit between the reinforcement units. When the plunger inclines, in a case in which the reinforcement units abut against an inner surface of the barrel, the inclination is prevented, but in a case in which the plunger inclines toward the portion with no reinforcement unit, the inclination of the plunger cannot be inhibited sufficiently.

One object of certain embodiments described herein is to provide a plunger for a syringe in which inclination of the plunger inside a barrel is inhibited after mounting a syringe on a gasket and that is capable of allowing the plunger to be mounted on the gasket without causing liquid leakage due to the inclination of the plunger. Another objection of certain embodiments is to provide a pre-filled syringe including the plunger.

In one embodiment, a plunger for a syringe includes: a gasket mounting portion provided at an upper end of the plunger; a disk positioned at a lower end of the gasket mounting portion; a shaft extending downward from the disk; and a pressing portion provided at a lower end portion of the shaft, wherein the shaft includes a plurality of slats extending downward from the disk, and the plunger includes a plunger inclination-prevention unit which is provided at a leading end of the shaft and is configured to prevent the plunger from inclining inside a barrel, and the plunger inclination-prevention unit includes an axially inclined plate that has a first end disposed on the disk, extending obliquely downward with respect to a central axis of the shaft, and having a second end disposed on any one of the slats, and the axially inclined plate has an outer edge positioned on a vertical line of an outer edge of the disk or about the vertical line, the axially inclined plate being provided between all the adjacent slats.

In another embodiment, a pre-filled syringe includes: the aforementioned plunger; and a drug pre-filled barrel, wherein the drug pre-filled barrel includes a sealed leading end; a barrel main body including a flange provided at a base end of the barrel main body; a gasket that is stored inside the base end of the barrel main body and on which the plunger for a syringe is mountable; and a drug stored inside the barrel main body.

DESCRIPTION OF EMBODIMENTS

Certain embodiments of a plunger for a syringe and a pre-filled syringe of the will be described below with reference to the drawings.

According to one embodiment, a pre-filled syringe 1 includes a drug pre-filled barrel 2 and a plunger 3 for a syringe.

Figure 1:
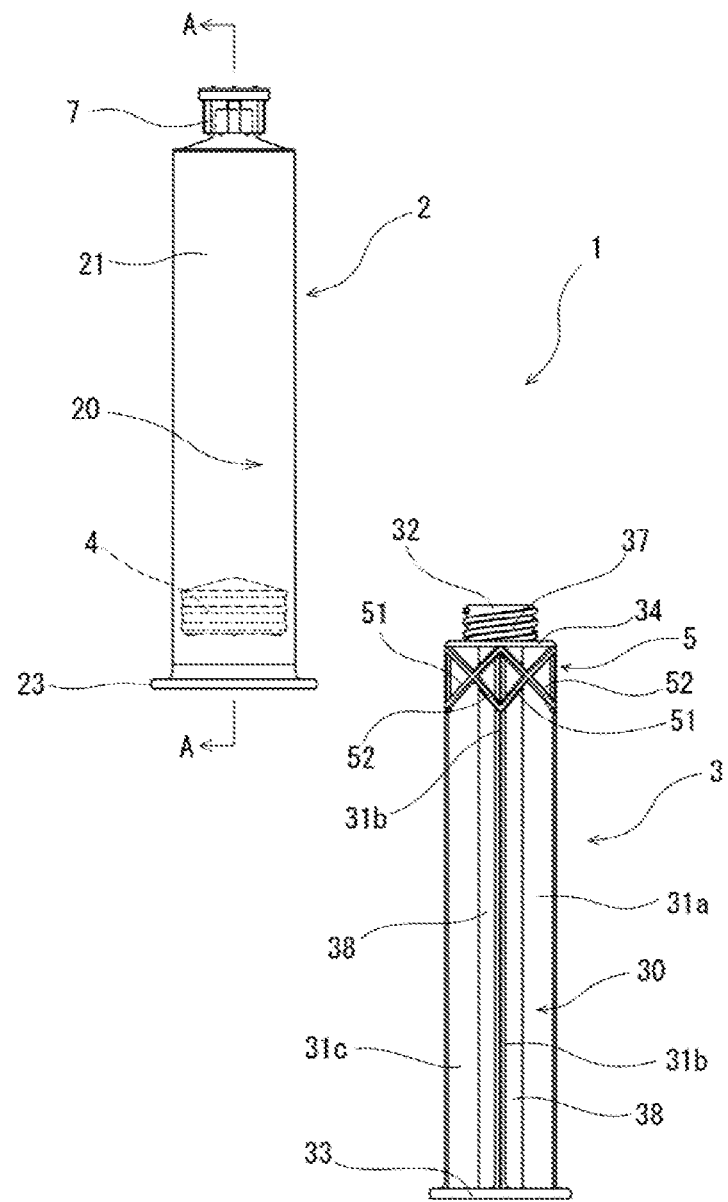
FIG. 1 is a front view of a pre-filled syringe according to an embodiment.
Figure 2:
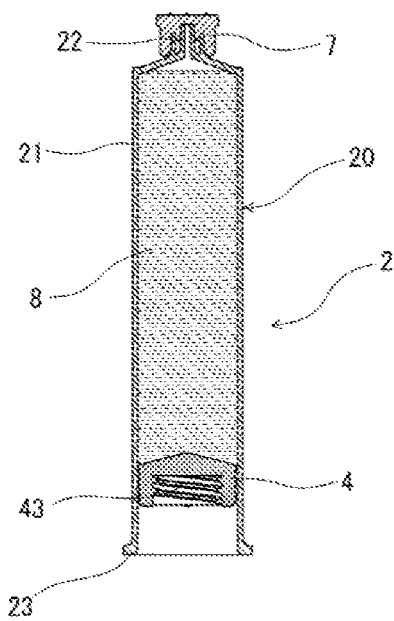
FIG. 2 is a cross-sectional view of a drug pre-filled barrel illustrated in FIG. 1, taken along line A-A.
Figure 3:
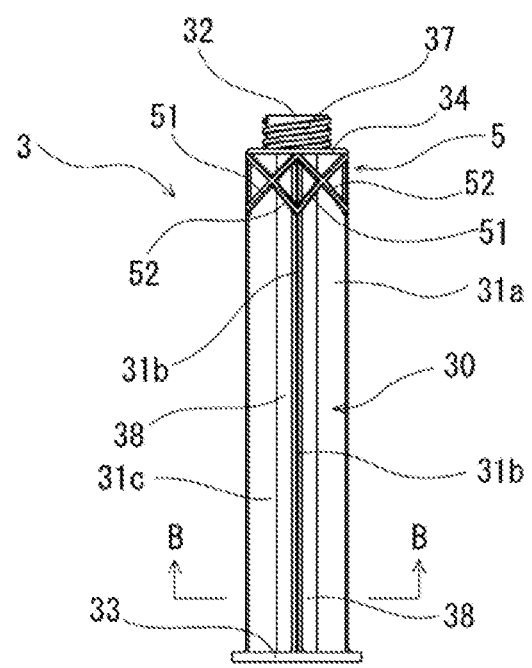
FIG. 3 is a front view of a plunger for a syringe according to an embodiment
Figure 4:
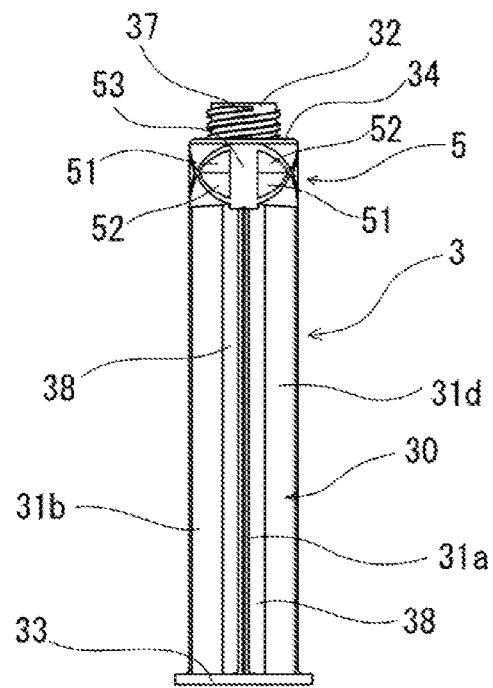
FIG. 4 is a right-side view of the plunger for a syringe illustrated in FIG. 3.

In the pre-filled syringe 1 according to an embodiment illustrated in FIGS. 1 and 2, the plunger 3 for a syringe is not mounted on the drug pre-filled barrel 2, and the plunger 3 for a syringe is to be mounted on the drug pre-filled barrel 2 when used.

The plunger 3 for a syringe includes a gasket mounting portion 32 provided at an upper end (distal end) of the plunger 3 for a syringe, a disk 34 located at a lower end (proximal end) of the gasket mounting portion 32, a shaft 30 extending downward (proximally) from the disk 34, and a pressing portion 33 provided at a lower end portion (proximal end portion) of the shaft 30. The shaft 30 has three or more slats 31a, 31b, 31c, and 31d extending downward from the disk 34. The plunger 3 has a plunger inclination-prevention unit 5 that is provided at a leading end of the shaft 30 and configured to prevent the plunger from inclining inside the barrel. The plunger inclination-prevention unit 5 includes axially inclined plates (axially inclined sectored plates) 51 and 52 each of which has a first end disposed on the disk 34, extending obliquely downward with respect to a central axis 35 of the shaft 30 by a predetermined length, and having a second end disposed on any one of the slats 31a, 31b, 31c, or 31d. Outer edges of the axially inclined sectored plates 51 and 52 are positioned on a vertical line of an outer edge of the disk 34 or about the vertical line (desirably, slightly inside the vertical line), and the axially inclined sectored plates 51 and 52 are provided between all the adjacent slats 31a, 31b, 31c, and 31d.

As illustrated in FIGS. 1 and 2, the drug pre-filled barrel 2 includes a sealed nozzle 22, a barrel main body 20 that includes a flange 23 provided at a base end of the barrel main body 20, a gasket 4 that is housed inside the base end of the barrel main body 20 and on which the plunger 3 for a syringe can be mounted, and a Drug 8 stored in the barrel main body 20. In this embodiment, a sealing member 7 is formed by a detachable sealing cap 7. It should be noted that the sealing member may be a peelable film-like member that seals a leading end surface of the nozzle 22.

The barrel main body 20 is a tubular body that includes a transparent or translucent material, preferably, a material having low oxygen permeability and water vapor permeability.

The barrel main body 20 includes a barrel body section 21; the nozzle 22 provided at a leading end of the barrel body section 21; and the flange 23 provided at a rear end of the barrel body section 21.

The barrel body section 21 is a substantially tubular portion that houses the gasket 4 in a liquid-tight and slidable manner. The nozzle 22 is a tubular portion having a diameter smaller than that of the barrel body section 21. The leading end of the barrel body section 21 is tapered having a diameter decreasing toward the nozzle 22. As illustrated in FIGS. 1 and 2, the flange 23 has an arcuate outer edge formed so as to protrude in a perpendicular direction from the entire circumference of the rear end of the barrel body section 21. In other words, the flange is shaped like an extended play record with an inner part missing.

As illustrated in FIG. 2, the nozzle 22 includes a nozzle body section and a collar formed concentrically with the nozzle body section. The nozzle body section is provided at the leading end of the barrel main body 20 and includes an opening at the leading end for discharging a medicinal solution and the like in the barrel. Furthermore, the nozzle body section is tapered, having a diameter decreasing toward the leading end. The collar is formed in a cylindrical shape so as to surround the nozzle body section concentrically.

Examples of a material for forming the barrel main body 20 include various types of resin such as polypropylene, polyethylene, polystyrene, polyamide, polycarbonate, polyvinyl chloride, poly-(4-methylpentene-1), acrylic resin, acrylonitrile-butadiene-styrene copolymers, polyesters such as polyethylene terephthalate, cyclic polyolefin polymers, and cyclic olefin copolymers. Among these examples, resin such as polypropylene, cyclic polyolefin polymers and cyclic olefin copolymers are preferable because those materials have heat resistance and are capable of easily forming the barrel main body 20. In regard to a material for forming the barrel 2, preferred examples include, especially, cyclic polyolefin polymers and cyclic olefin copolymers because those materials have high transparency and heat resistance so that a medicinal solution filled inside the barrel 2 can be visually confirmed from the outside and the barrel 2 can endure autoclave sterilization.

As illustrated in FIGS. 1 and 2, the sealing member (sealing cap) 7 has a closed end, a tubular body section, and a nozzle-housing unit formed inside the tubular portion. The nozzle-housing unit includes a nozzle leading end-housing unit that houses a leading end of the nozzle body section, and a collar leading end-housing unit that houses a leading end of the collar. In an outer surface of the sealing cap 7, an anti-slip protrusion is formed. In regard to a material for forming the sealing member (sealing cap), elastic materials are preferable, for example, natural rubber; synthetic rubber such as isoprene rubber, butyl rubber, butadiene rubber, fluoro-rubber, and silicone rubber; and thermoplastic elastomers such as olefin elastomers, and styrene elastomers.

The gasket 4 is housed inside the base end of the barrel main body 20, specifically, at a position which is closer to the leading end than an opening in the base end of the barrel main body 20 by a predetermined length. A distance between a base end of the gasket 4 and the base end of the barrel main body 20 is preferably from 5 to 30 mm, more preferably, from 10 to 15 mm. The distance between the base end of the gasket 4 and the base end of the barrel main body 20 is preferably equal to or more than a half of an axial length of the plunger inclination-prevention unit 5 of the plunger 3, as described below.

As illustrated in FIGS. 1 and 2, the gasket 4 of this embodiment includes a tubular body section extending with a substantially uniform outer diameter, and a tapered closing portion extending toward the leading end from the body section. In addition, a plurality of annular ribs (three in this embodiment, but if there are two or more ribs, any number is employable as long as the ribs satisfy liquid-tightness and slidability) is formed on an outer surface of the body section. These ribs contact with an inner surface of the barrel main body 20 in a liquid-tight manner.

The gasket 4 includes a recess that is provided inside the tubular body section and extends toward the leading end from the opening in the rear end. This recess is capable of housing the gasket mounting portion 32 of the plunger 3. Furthermore, in an inner surface of the recess (an inner surface of the tubular body section), an in-gasket screwing unit 43 is formed. The in-gasket screwing unit 43 can be screwed with an in-plunger screwing unit 37 formed in an outer surface of the gasket mounting portion 32 of the plunger 3. As both of the screwing units are screwed together, the plunger 3 does not separate from the gasket 4. It should be noted that the plunger 3 is to be attached when used.

Preferable examples of a material for forming the gasket 4 include elastic rubber (for example, butyl rubber, latex rubber, and silicone rubber), and synthetic resins (for example, styrene elastomers such as SBS elastomers and SEBS elastomers, and olefinic elastomers such as ethylene-α olefin copolymer elastomers).

Examples of the medicinal solution 8 to be filled in a space formed by the barrel main body 20, the gasket 4, and the sealing member 7 include contrast media, highly concentrated sodium chloride injection solutions, minerals, sodium heparin solutions, nitroglycerin, isosorbide dinitrate, cyclosporine, benzothiazepine agents, antibiotics, vitamins (multiple vitamins), various amino acids, antithrombotic agents such as heparin, insulin, antitumor agents, analgesics, cardiotonic agents, intravenous anesthetic agents, antiparkinsonian agents, anti-ulcer agents, adrenocortical hormone agents, arrhythmia agents, corrective electrolytes, antiviral agents, and immunostimulants. The medicinal solution 8 to be filled may be, particularly, one that is administered when the pre-filled syringe 1 (barrel 2) is mounted on automatic administration equipment such as an injector or a syringe pump including a flange-housing unit into which the flange 23 of the barrel main body 20 is inserted. Examples of the medicinal solution 8 to be administered in this way include contrast media for angiography.

As illustrated in FIGS. 3 to 19, the plunger 3 includes the gasket mounting portion 32 provided at the upper end of the plunger 3, the disk 34 placed at the lower end of the gasket mounting portion 32, the shaft 30 extending downward from the disk 34, and the pressing portion 33 provided about the lower end of the shaft 30.

Figure 5:
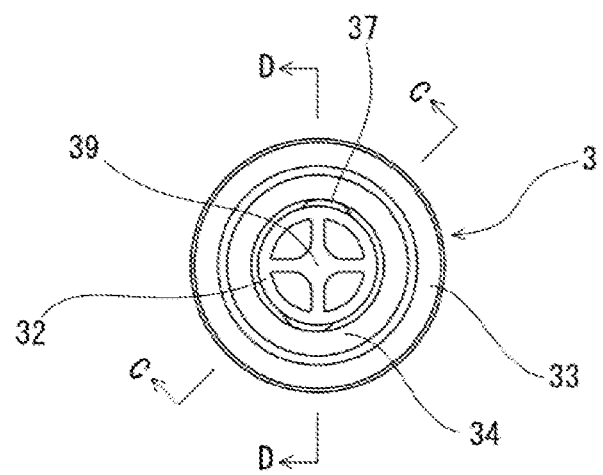
FIG. 5 is an enlarged plan view of the plunger for a syringe illustrated in FIG. 3.

The gasket mounting portion 32 is a protrusion provided at the leading end of the plunger 3. The gasket mounting portion 32 protrudes upward (toward the leading end) from about the center of the disk 34. The gasket mounting portion 32 is desirably a tubular portion but may be a rod-like portion. In this embodiment, as illustrated in FIG. 5, the gasket mounting portion 32 is a tubular portion having a cross-shaped reinforcement unit 39 on the inside.

In the outer surface of the gasket mounting portion 32, the in-plunger screwing unit 37 to be screwed with the in-gasket screwing unit 43 of the gasket 4 is provided. The in-plunger screwing unit 37 is formed by a helical rib. The in-plunger screwing unit 37 includes the helical rib having two folds so as to correspond to the helical screwing unit 43 of the gasket 4. Note that the helical rib may have a single fold. In the syringe of this embodiment, as the plunger 3 rotates, both of the gasket 4 and the plunger 3, which are to be described later, are put into a mounted state.

The disk 34 is a plate that is a substantially exact circle and has a diameter slightly smaller than an inner diameter of the barrel main body 20. The gasket mounting portion 32 is provided in such a manner that the center lies on a central axis of the disk 34.

Figure 6:
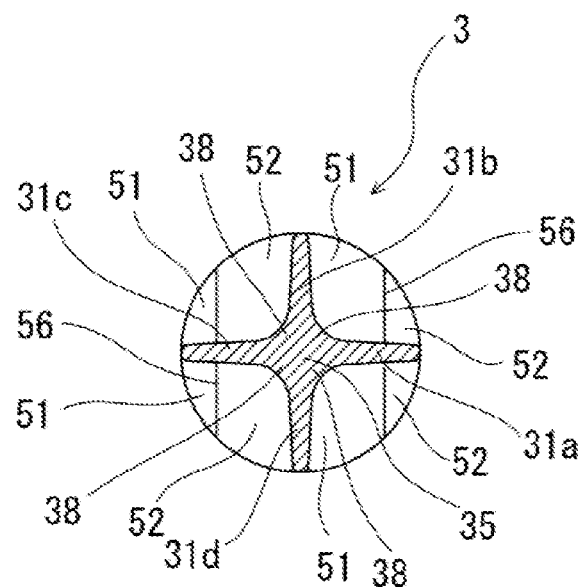
FIG. 6 is an enlarged cross-sectional view taken along line B-B of FIG. 3.

The shaft 30 has three or more slats 31a, 31b, 31c, and 31d (four in this embodiment) extending downward from the disk 34. As illustrated in FIG. 6, the shaft 30 of this embodiment has four slats 31a, 31b, 31c, and 31d extending radially and equiangularly (specifically, at an interval of 90 degrees) with respect to the central axis 35 of the shaft 30. Furthermore, in the shaft 30 of this embodiment, a joint portion of each of the slats 31a, 31b, 31c, and 31d is provided with an axial reinforcement unit 38 extending throughout the entire length of the slats. Therefore, the shaft 30 has a thick central portion, or a thick shaft axis.

At the rear end of the shaft 30, the pressing portion 33 is provided. The pressing portion 33 is formed in a disk shape and is used as a plunger pressing portion. The pressing portion 33 of this embodiment is a disk-shaped member having a diameter larger than that of the aforementioned disk 34.

Each of the slats 31a, 31b, 31c, and 31d has a first end connected to the disk 34 and a second other end connected to the pressing portion 34. In this embodiment, the slats 31a, 31b, 31c, and 31d extend in parallel to the central axis 35 of the shaft 30 with substantially uniform width and thickness from the first end to the second end. Therefore, the slats 31a, 31b, 31c, and 31d are perpendicular to the disk 34 and the pressing portion 34. Furthermore, an outer edge of the shaft 30, or outer edges of the slats 31a, 31b, 31c, and 31d are positioned on the vertical line of the outer edge of the disk 34 or about the inner side of the vertical line.

The plunger 3 has the plunger inclination-prevention unit 5 that is provided at the leading end of the shaft 30 and configured to prevent the plunger from inclining inside the barrel main body 20.

Figure 9:
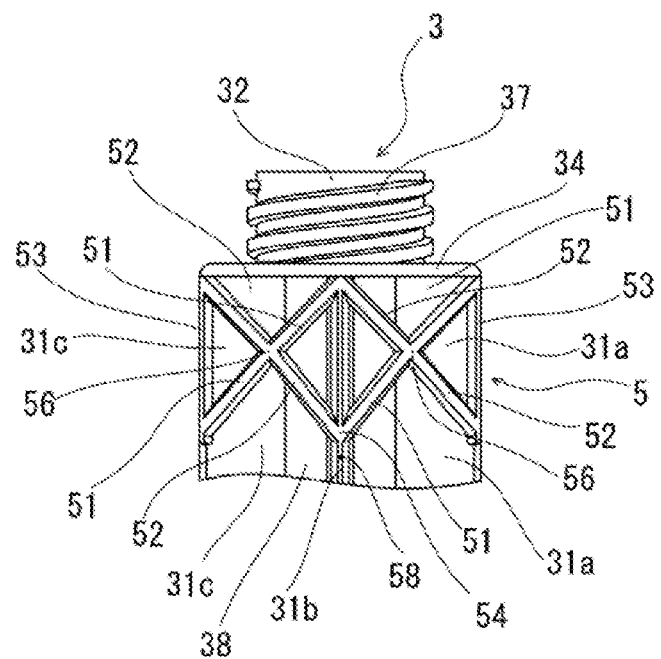
FIG. 9 is an enlarged view (enlarged front view) of a leading end of the plunger for a syringe illustrated in FIG. 3.
Figure 10:
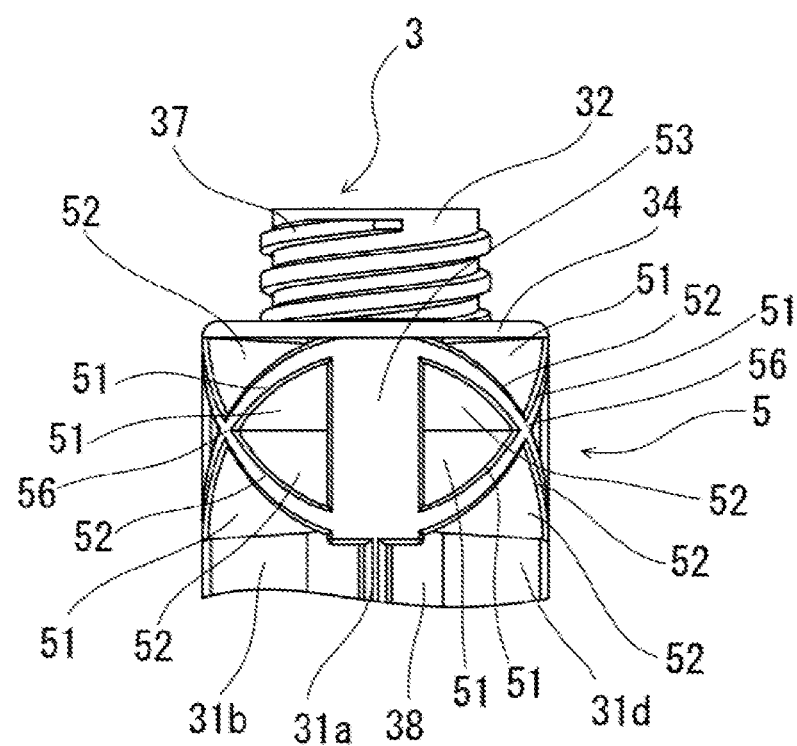
FIG. 10 is an enlarged view (enlarged right side view) of the leading end of the plunger for a syringe illustrated in FIG. 4.

Particularly, in the plunger 3 of this embodiment, as illustrated in FIGS. 3 to 10, especially, in FIGS. 9 and 10, the plunger inclination-prevention unit 5 includes the axially inclined sectored plate (first directionally inclined sectored plate) 51 that has a first end disposed on the disk 34 and the upper end of any one of the slats, extending obliquely downward with respect to the central axis 35 of the shaft 30 by a predetermined length, and having a second end disposed on another slat adjacent to the aforementioned slat having the first end.

Specifically, the plunger inclination-prevention unit 5 includes the first axially inclined sectored plate (first directionally inclined sectored plate, or first directionally inclined sectored plate with an initial end-on-disk slat connection) 51 that has a first end (an initial end) disposed on an intersection between the disk 34 and the first slat 31a (that is, a lower surface of the disk 34 and the upper end of the first slat 31a), extending obliquely downward with respect to the central axis 35 of the shaft 30 by a predetermined length, and having a second end (a terminal end) disposed on the second slat 31b adjacent to the first slat 31a. In order to allow the first directionally inclined sectored plate 51 to connect the first slat 31a with the adjacent second slat 31b in an oblique manner, the sectored plate 51 is provided between the first slat 31a and the adjacent second slat 31b throughout the entire axial length.

Similarly, the plunger inclination-prevention unit 5 includes the first directionally inclined axially inclined sectored plate (first directionally inclined sectored plate) 51 that has a first end (an initial end) disposed on an intersection between the disk 34 and the second slat 31b (that is, the lower surface of the disk 34 and the upper end of the second slat 31b), extending obliquely downward with respect to the central axis 35 of the shaft 30 by a predetermined length, and having a second end (a terminal end) disposed on the third slat 31c adjacent to the second slat 31b. In order to allow the first directionally inclined sectored plate 51 to connect the second slat 31b with the adjacent third slat 31c in an oblique manner, the sectored plate 51 is provided between the second slat 31b and the adjacent third slat 31c throughout the entire axial length.

Similarly, the plunger inclination-prevention unit 5 includes the first axially inclined sectored plate (first directionally inclined sectored plate) 51 that has a first end (an initial end) disposed on an intersection between the disk 34 and the third slat 31c (that is, the lower surface of the disk 34 and the upper end of the third slat 31c), extending obliquely downward with respect to the central axis 35 of the shaft 30 by a predetermined length, and having a second end (a terminal end) disposed on the fourth slat 31d adjacent to the third slat 31c. In order to allow the first directionally inclined sectored plate 51 to connect the third slat 31c with the adjacent fourth slat 31d in an oblique manner, the sectored plate 51 is provided between the third slat 31c and the adjacent fourth slat 31d throughout the entire axial length.

Similarly, the plunger inclination-prevention unit 5 includes the first axially inclined sectored plate (first directionally inclined sectored plate) 51 that has a first end (an initial end) disposed on an intersection between the disk 34 and the fourth slat 31d (that is, the lower surface of the disk 34 and the upper end of the fourth slat 31*d*), extending obliquely downward with respect to the central axis 35 of the shaft 30 by a predetermined length, and having a second end (a terminal end) disposed on the first slat 31*a* adjacent to the fourth slat 31*d*. In order to allow the first axially inclined sectored plate 51 to connect the fourth slat 31*d* with the adjacent first slat 31*a* in an oblique manner, the sectored plate 51 is provided between the fourth slat 31*d* and the adjacent first slat 31*a* throughout the entire axial length.

Figure 7:
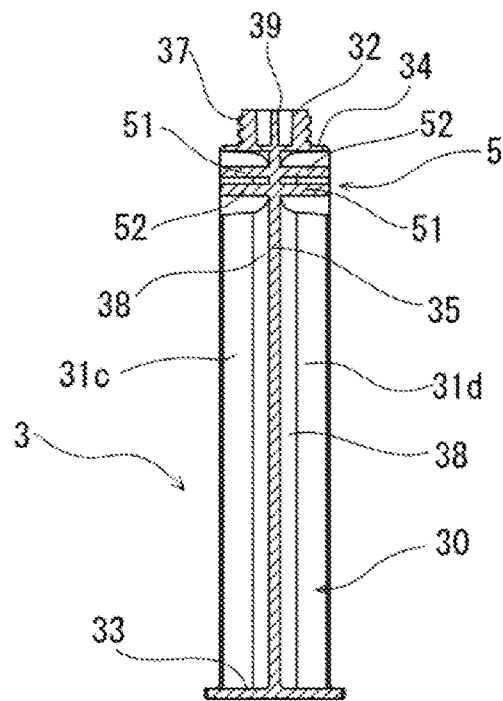
FIG. 7 is a cross-sectional view taken along line C-C of FIG. 5.
Figure 8:
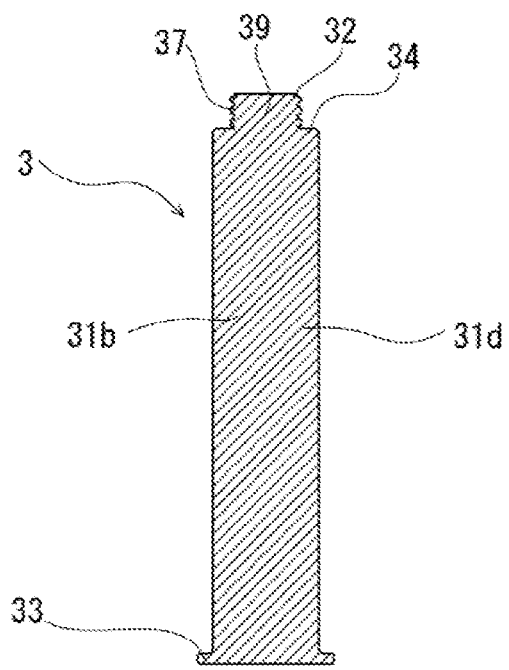
FIG. 8 is a cross-sectional view taken along line D-D in FIG. 5.

As described above, in the plunger 3, the axially inclined sectored plate (first directionally inclined sectored plate) 51 is provided between all the adjacent slats 31*a*, 31*b*, 31*c*, and 31*d*. Furthermore, as illustrated in FIGS. 6 and 7, the outer edge of the axially inclined sectored plate 51 is positioned on the vertical line of the outer edge of the disk 34 or about the inner side of the vertical line. Particularly, in the plunger 3 of this embodiment, the outer edge of the axially inclined sectored plate 51 is positioned substantially on the vertical line of the outer edge of the disk 34. Imagine a cylindrical body extending downward with an inner diameter equivalent to the outer edge of the disk 34. The outer edge of the sectored plate 51 is positioned on an inner surface of the imaginary cylindrical body. In other words, the outer edge of the sectored plate 51 does not protrude from the inner surface of the imaginary cylindrical body.

Furthermore, in this embodiment, the terminal end of the sectored plate 51 forms a terminal end of the plunger inclination-prevention unit 5. It is preferable that the axial length of the plunger inclination-prevention unit 5 (a distance from the disk 34 to a lower end of the plunger inclination-prevention unit 5) is 10 to 40 mm. Particularly, it is preferable that the distance is 20 to 30 mm.

Furthermore, in the plunger 3 of this embodiment, as illustrated in FIGS. 3 to 10, especially, in FIGS. 9 and 10, the plunger inclination-prevention unit 5 includes the axially inclined sectored plate (second directionally inclined sectored plate, or second directionally inclined sectored plate with an initial end-on-disk slat connection) 52 that has a first end disposed on the disk 34 and the upper end of any one of the slats, extending obliquely downward with respect to the central axis 35 of the shaft 30 by a predetermined length, having a second end disposed on another slat adjacent to the aforementioned slat having the first end, and inclining in a direction different from the first directionally inclined sectored plate 51. The first directionally inclined sectored plate 51 and the second directionally inclined sectored plate include an intersection 56. In this embodiment, a plurality of (two) axially inclined sectored plates is provided between the adjacent slats. In this embodiment, the first directionally inclined sectored plate 51 and the second directionally inclined sectored plate 52 are connected at a terminal end 54.

Specifically, the plunger inclination-prevention unit 5 includes the second axially inclined sectored plate (second directionally inclined sectored plate) 52 that has a first end (an initial end) disposed on an intersection between the disk 34 and the second slat 31*b* (that is, the lower surface of the disk 34 and the upper end of the second slat 31*b*), extending obliquely downward with respect to the central axis 35 of the shaft 30 by a predetermined length, and having a second end (a terminal end) disposed on the first slat 31*a* adjacent to the second slat 31*b*. The second axially inclined sectored plate (second directionally inclined sectored plate) 52 is inclined in a direction different from the first axially inclined sectored plate (first directionally inclined sectored plate) 51. Therefore, the second directionally inclined sectored plate 52 and the first directionally inclined sectored plate 51 intersect each other between the second slat 31*b* and the adjacent first slat 31*a*, including the intersection 56. In the plunger 3 of this embodiment, the terminal end of the first directionally inclined sectored plate 51 and that of the second directionally inclined sectored plate 52 are substantially coplanar in the shaft 30.

Similarly, the plunger inclination-prevention unit 5 includes the second axially inclined sectored plate (second directionally inclined sectored plate) 52 that has a first end (an initial end) disposed on an intersection between the disk 34 and the third slat 31*c* (that is, the lower surface of the disk 34 and the upper end of the third slat 31*c*), extending obliquely downward with respect to the central axis 35 of the shaft 30 by a predetermined length, and having a second end (a terminal end) disposed on the second slat 31*b* adjacent to the third slat 31*c*. The second directionally inclined sectored plate 52 and the first directionally inclined sectored plate 51 intersect each other between the third slat 31*c* and the second slat 31*b*, including the intersection 56.

Similarly, the plunger inclination-prevention unit 5 includes the second axially inclined sectored plate (second directionally inclined sectored plate) 52 that has a first end (an initial end) disposed on an intersection between the disk 34 and the fourth slat 31*d* (that is, the lower surface of the disk 34 and the upper end of the fourth slat 31*d*), extending obliquely downward with respect to the central axis 35 of the shaft 30 by a predetermined length, and having a second end (a terminal end) disposed on the third slat 31*c* adjacent to the fourth slat 31*d*. The second directionally inclined sectored plate 52 and the first directionally inclined sectored plate 51 intersect each other between the fourth slat 31*d* and the third slat 31*c*, including the intersection 56.

Similarly, the plunger inclination-prevention unit 5 includes the second axially inclined sectored plate (second directionally inclined sectored plate) 52 that has a first end (an initial end) disposed on an intersection between the disk 34 and the first slat 31*a* (the lower surface of the disk 34 and the upper end of the first slat 31*a*), extending obliquely downward with respect to the central axis 35 of the shaft 30 by a predetermined length, and having a second end (a terminal end) disposed on the fourth slat 31*d* adjacent to the first slat 31*a*. The second directionally inclined sectored plate 52 and the first directionally inclined sectored plate 51 intersect each other between the first slat 31*a* and the fourth slat 31*d*, including the intersection 56.

Furthermore, as illustrated in FIGS. 6 and 7, the outer edge of the axially inclined sectored plate 52 is positioned on the vertical line of the outer edge of the disk 34 or about the inner side of the vertical line. Particularly, in the plunger 3 of this embodiment, the outer edge of the axially inclined sectored plate 52 is positioned substantially on the vertical line of the outer edge of the disk 34. Imagine a cylindrical body extending downward with an inner diameter equivalent to the outer periphery of the disk 34. The outer edge of the sectored plate 52 is positioned on an inner surface of the imaginary cylindrical body. In other words, the outer edge of the sectored plate 52 does not protrude from the inner surface of the imaginary cylindrical body.

Furthermore, in the plunger 3 of this embodiment, as illustrated in FIGS. 3 to 10, particularly, in FIG. 10, the plunger inclination-prevention unit 5 includes an arcuate plate 53 having a first disposed on the disk 34 and extending downward along the shaft 30 with a predetermined width. The arcuate plate 53 is formed in pairs so as to face each other across the central axis of the plunger. The initial end and the terminal end of the inclined sectored plate 51 are connected to the initial end and the terminal end of inclined sectored plate 52, respectively, in the arcuate plate 53.

The arcuate plate 53 has the first end disposed on the disk 34 and extends downward along the outer edge of each of the first slat 31a and the third slat 31c with a predetermined width. The width of the arcuate plate 53 is preferably about 3/100 to 10/100 of an outer periphery of the disk 34. Furthermore, it is preferable that the axial length of the arcuate plate 53 (a distance from the disk 34 to a terminal end of the arcuate plate 53) is 10 to 40 mm. Particularly, it is preferable that the distance is 20 to 30 mm. Still further, it is preferable that the outer edge of the arcuate plate 53 is positioned substantially on the vertical line or the inner side of the outer edge of the disk 34. Particularly, it is preferable that the outer edge of the arcuate plate 53 is positioned substantially on the vertical line of the outer edge of the disk 34.

Figure 31:
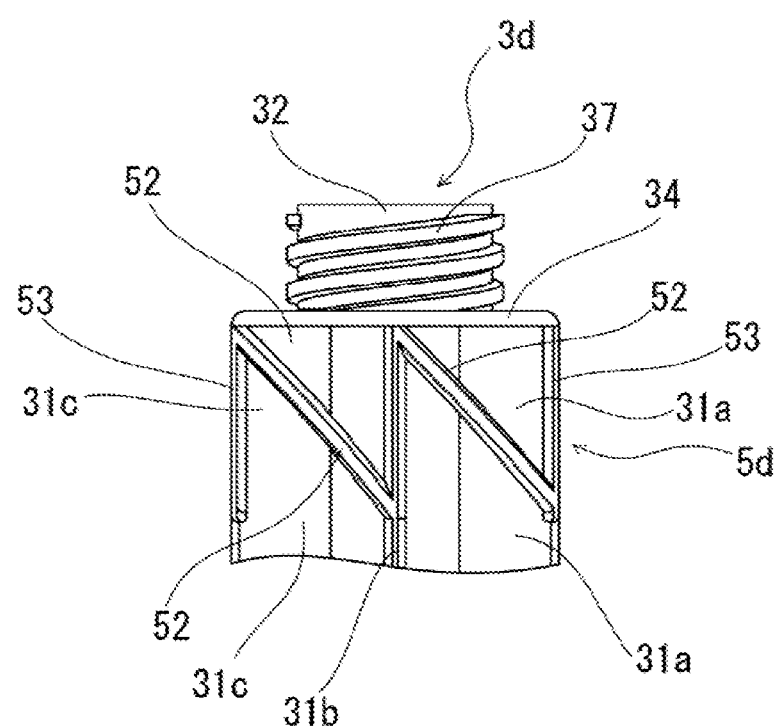
FIG. 31 is an enlarged front view of a leading end of a plunger for a syringe according to another embodiment.

It should be noted that the plunger inclination-prevention unit may be provided with one axially inclined sectored plate between adjacent slats such as a plunger inclination-prevention unit 5d included in a plunger 3d for a syringe according to an embodiment illustrated in FIG. 31. The plunger 3d for a syringe according to this embodiment includes a single axially inclined sectored plate (second directionally inclined sectored plate) with an initial end-on-disk slat connection) 52 that has a first end disposed on the disk 34 and the upper end of any one of the slats, extending obliquely downward with respect to the central axis 35 of the shaft 30 by a predetermined length, and having a second end disposed on another slat adjacent to the aforementioned slat having the first end. It should be noted that the plunger 3d may include a single axially inclined sectored plate (first directionally inclined sectored plate with an initial end-on-disk slat connection) 51 that has the first end disposed on the disk 34 and the upper end of any one of the slats, extending obliquely downward with respect to the central axis 35 of the shaft 30 by a predetermined length, and having a second end disposed on another slat adjacent to the aforementioned slat having the first end. Alternatively, the plunger 3d may include the first directionally inclined sectored plate 51 and the second directionally inclined sectored plate 52 provided alternately in a circumferential direction. Even in such plungers of these embodiments, the axially inclined sectored plate is disposed between all the adjacent slats 31a, 31b, 31c, and 31d.

A preferable example of a material included in the plunger 3 includes hard or semi-hard resin such as highly concentrated polyethylene, polypropylene, polystyrene, and polyethylene terephthalate. Furthermore, in the plunger 3 of this embodiment, it is preferable that a resin gate position 58 at the time of molding is provided at a position on the outer edge of each slat that is closer to the lower end of the plunger 3 than the lower end of each sectored plate. With such a configuration, it is possible to perform good injection molding.

Figure 11:
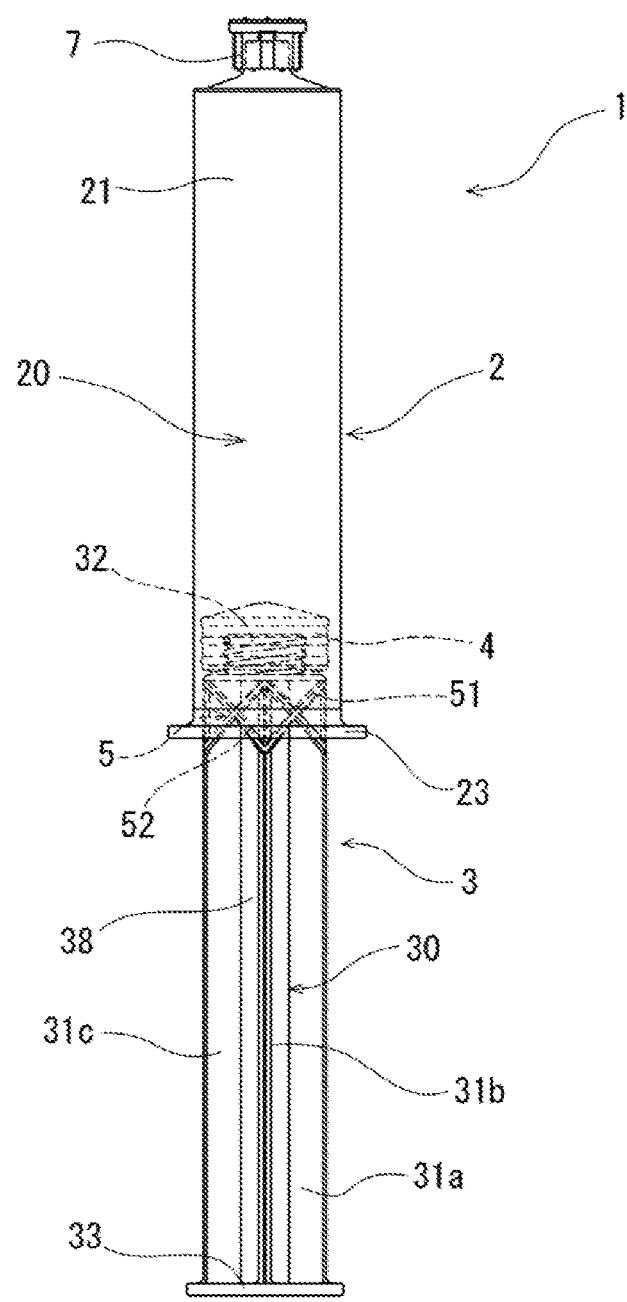
FIG. 11 is a front view of the pre-filled syringe with the plunger for a syringe being mounted on the drug pre-filled barrel.
Figure 12:
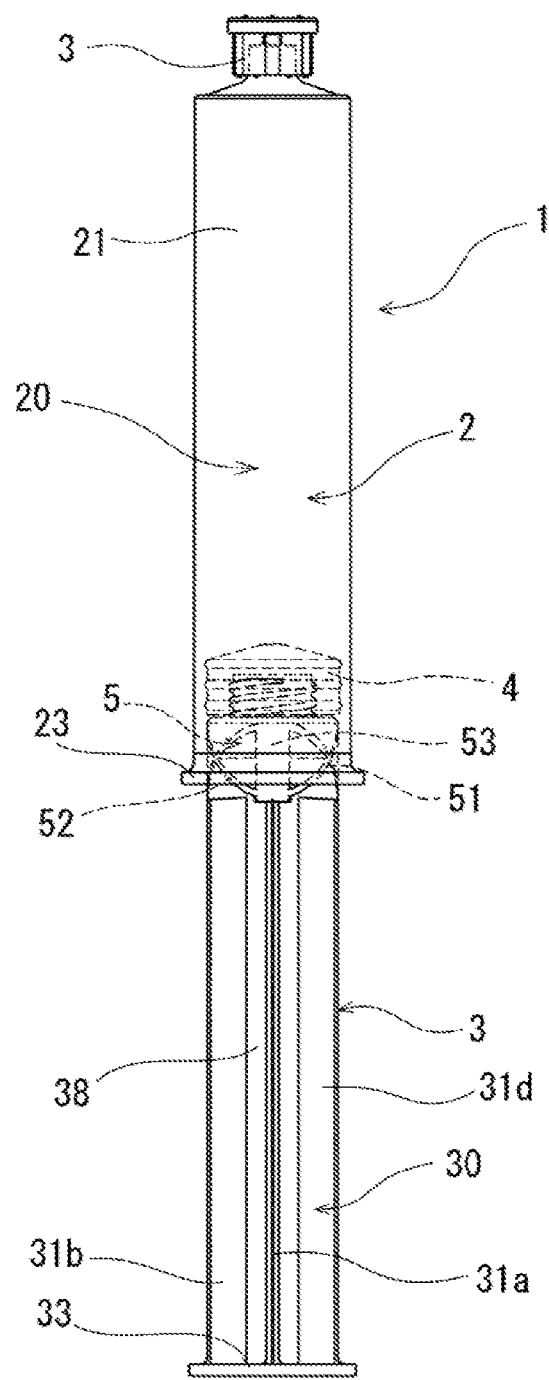
FIG. 12 is a right-side view of the pre-filled syringe illustrated in FIG. 11.
Figure 13:
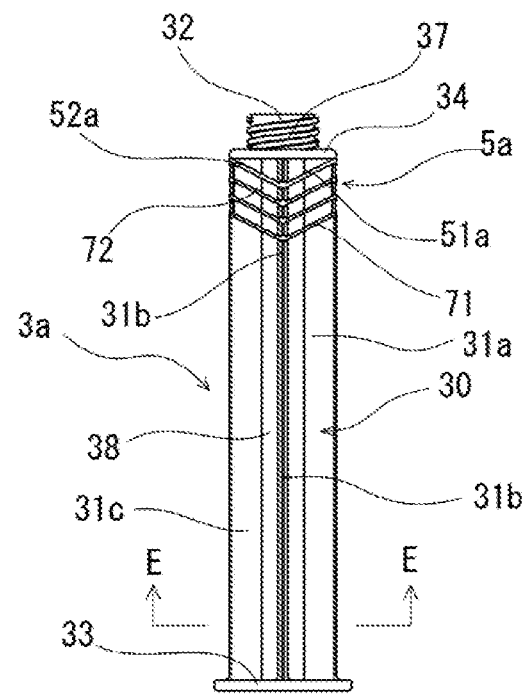
FIG. 13 is a front view of a plunger for a syringe according to another embodiment.
Figure 14:
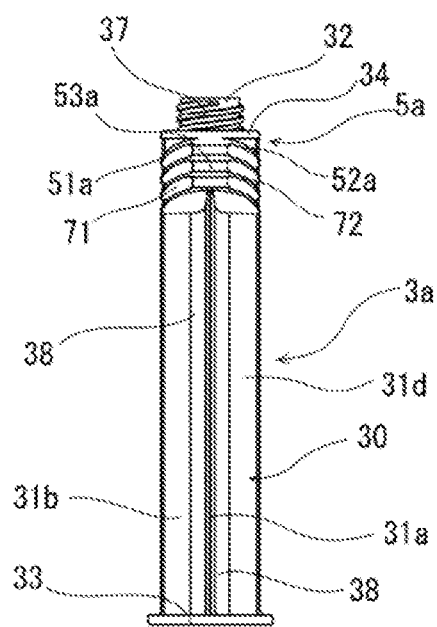
FIG. 14 is a right-side view of the plunger for a syringe illustrated in FIG. 13.
Figure 15:
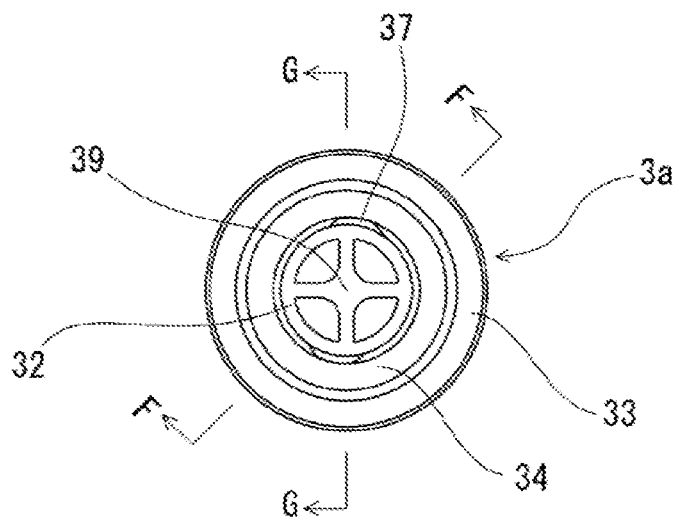
FIG. 15 is an enlarged plan view of the plunger for a syringe illustrated in FIG. 13.

As illustrated in FIGS. 11 and 12, the pre-filled syringe of this embodiment is used after the plunger 3 for a syringe is mounted on the drug pre-filled barrel 2. In the pre-filled syringe of this embodiment, as illustrated in FIGS. 11 and 12, when the plunger 3 for a syringe is mounted on the drug pre-filled barrel 2, at least a part of the plunger inclination-prevention unit 5 closer to the leading end than a central portion thereof is housed inside the barrel main body 20. Particularly, in mounting the plunger, it is preferable that a half or more of the axial length of the plunger inclination-prevention unit 5 of the plunger 3 for a syringe is housed inside the barrel main body 20. Such a configuration leads to an excellent inclination-preventing function of the plunger inclination-prevention unit 5.

The plunger inclination-prevention unit 5 in the plunger 3 is not limited to the aforementioned embodiment. For example, a plunger inclination-prevention unit 5a provided in a plunger 3a for a syringe illustrated in FIGS. 13 to 20 may also be employable. A difference between the plunger 3a for a syringe of this embodiment and the plunger 3 for a syringe of the aforementioned embodiment is the configuration of the plunger inclination-prevention unit.

Figure 19:
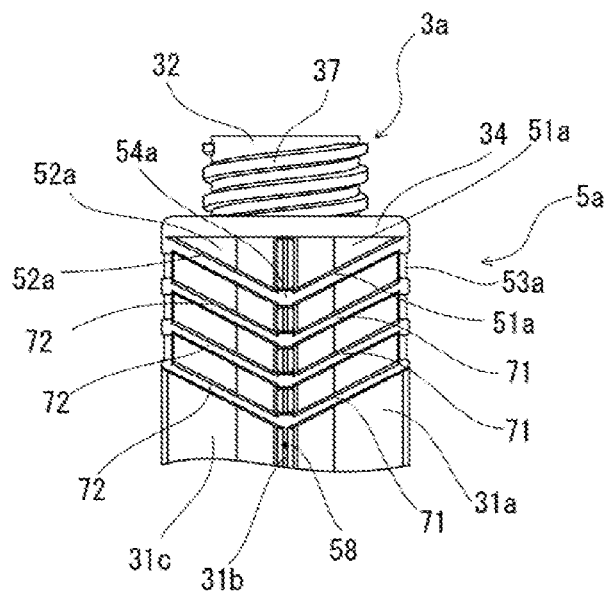
FIG. 19 is an enlarged view (enlarged front view) of a leading end of the plunger for a syringe illustrated in FIG. 13.
Figure 20:
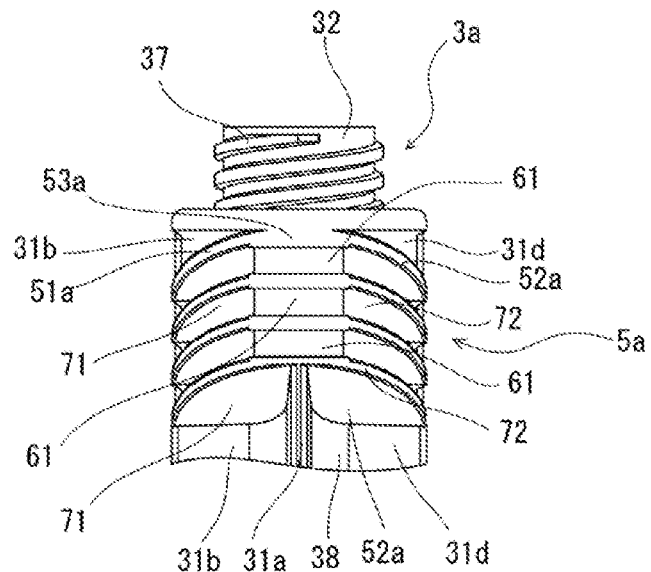
FIG. 20 is an enlarged view (enlarged right side view) of the leading end of the plunger for a syringe illustrated in FIG. 14.
Figure 21:
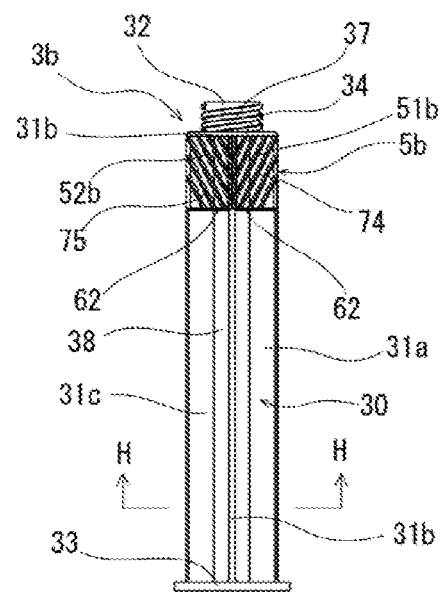
FIG. 21 is a front view of a plunger for a syringe according to another embodiment.
Figure 22:
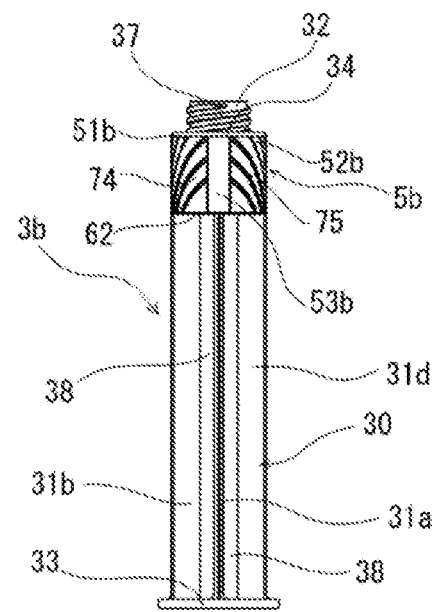
FIG. 22 is a right-side view of the plunger for a syringe illustrated in FIG. 21.
Figure 23:
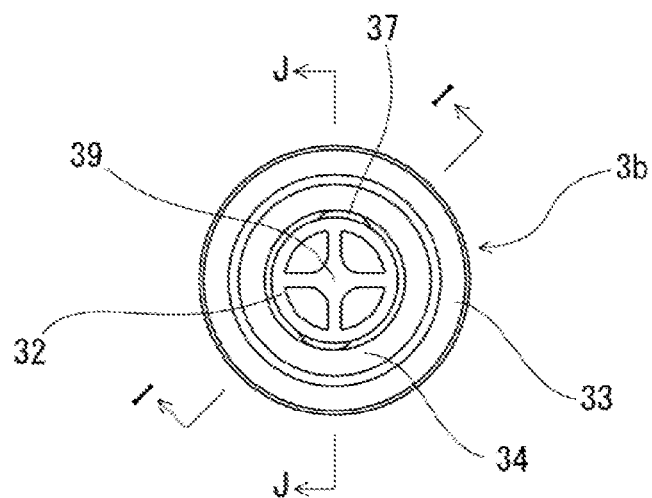
FIG. 23 is an enlarged plan view of the plunger for a syringe illustrated in FIG. 21.
Figure 24:
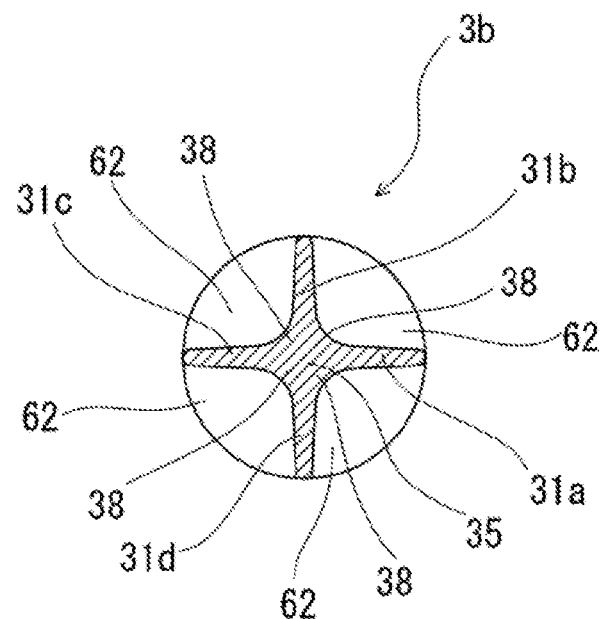
FIG. 24 is an enlarged cross-sectional view taken along line H-H of FIG. 21.
Figure 25:
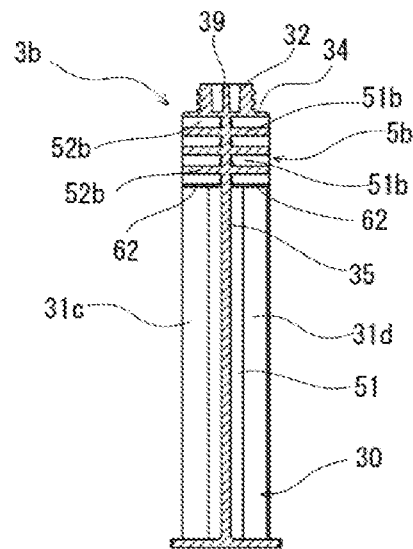
FIG. 25 is a cross-sectional view taken along line I-I of FIG. 23.
Figure 26:
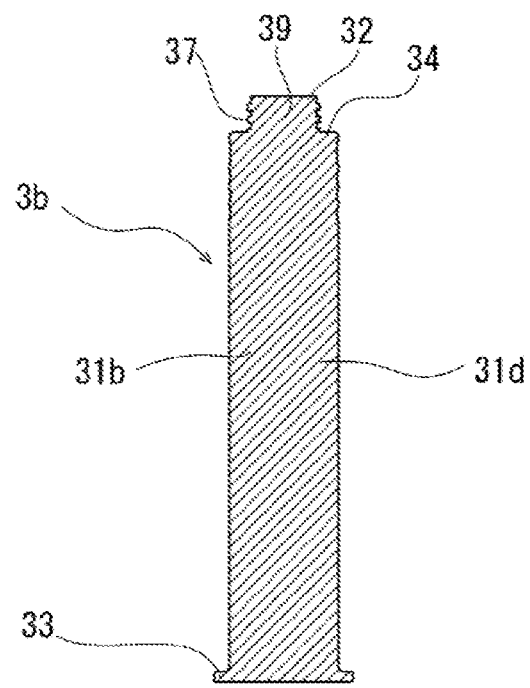
FIG. 26 is a cross-sectional view taken along line J-J in FIG. 23.

In the plunger 3a of this embodiment, as illustrated in FIGS. 13 to 20, especially, in FIGS. 19 and 20, the plunger inclination-prevention unit 5a includes an axially inclined sectored plate (first directionally inclined sectored plate, or first directionally inclined sectored plate with an initial end-on-disk slat connection) 51a that has a first end disposed on the disk 34 and the upper end of any one of the slats, extending obliquely downward with respect to the central axis 35 of the shaft 30 by a predetermined length, and having a second end disposed on another slat adjacent to the aforementioned slat having the first end.

Furthermore, in the plunger inclination-prevention unit 5a of this embodiment, between two slats adjacent to two slats that includes the axially inclined sectored plate (first directionally inclined sectored plate) 51a, there is provided an axially inclined sectored plate (second directionally inclined sectored plate, or second directionally inclined sectored plate with an initial end-on-disk slat connection) 52a that has the first end disposed on the disk 34 and the upper end of any one of the slats, extending obliquely downward with respect to the central axis 35 of the shaft 30 by a predetermined length, and having a second end disposed on another slat adjacent to the aforementioned slat having the first end. The second directionally inclined sectored plate 52a inclines in a direction different from the first directionally inclined sectored plate 51a.

Furthermore, in the plunger inclination-prevention unit 5a of this embodiment, between two slats adjacent to the two slats that includes the axially inclined sectored plate (the first directionally inclined sectored plate) 52a, the first directionally inclined sectored plate 51a is disposed. Still further, between two slats adjacent to the two slats that includes the axially inclined sectored plate (the first directionally inclined sectored plate) 51a, the axially inclined sectored plate (the second directionally inclined sectored plate) 52a is disposed.

The plunger inclination-prevention unit 5a of this embodiment has either one of the first directionally inclined sectored plate 51a or the second directionally inclined sectored plate 52a between two adjacent slats, and the first directionally inclined sectored plate 51a and the second directionally inclined sectored plate 52a are arranged alternately in the circumferential direction.

Specifically, the plunger inclination-prevention unit 5a includes the first axially inclined sectored plate (first directionally inclined sectored plate) 51a that has the first end (an initial end) disposed on an intersection between the disk 34 and the first slat 31a (that is, the lower surface of the disk 34 and the upper end of the first slat 31a), extending obliquely downward with respect to the central axis 35 of the shaft 30 by a predetermined length, and having a second end (a terminal end) disposed on the second slat 31b adjacent to the first slat 31a. Even in this embodiment, in order to allow the first directionally inclined sectored plate 51a to connect the first slat 31a with the adjacent second slat 31b in an oblique manner, in a part provided with the sectored plate 51a, a reinforcement unit (sectored plate 51a) is provided between the first slat 31a and the adjacent second slat 31b throughout the entire axial length.

In addition, the plunger inclination-prevention unit 5a of this embodiment includes a first axially inclined sectored plate (first directionally inclined sectored plate, or first directionally inclined sectored plate with an initial end-on-slat) 71 that is disposed below the first directionally inclined sectored plate 51a, having a first end (an initial end) disposed on an outer edge of the first slat 31a below the disk 34 by a predetermined length, extending obliquely downward with respect to the central axis 35 of the shaft 30 by a predetermined length, and having a second end (a terminal end) disposed on the second slat 31b adjacent to the first slat 31a. In this embodiment, a plurality of first directionally inclined sectored plates 71 is provided in the axial direction. The first axially inclined sectored plate 51a and the first axially inclined sectored plates 71 are substantially parallel to each other, and they are separated from each other by a substantially equidistance.

Similarly, between the first slat 31a and the second slat 31b and between the third slat 31c and the fourth slat 31d opposing each other across the central axis 35 of the shaft 30, there are provided the first directionally inclined sectored plate 51a and the plurality of first axially inclined sectored plates (first directionally inclined sectored plates) 71.

Furthermore, the plunger inclination-prevention unit 5a includes the second axially inclined sectored plate (second directionally inclined sectored plate) 52a that has a first end (an initial end) disposed on an intersection between the disk 34 and the third slat 31c (the lower surface of the disk 34 and the upper end of the third slat 31c), extending obliquely downward with respect to the central axis 35 of the shaft 30 by a predetermined length, and having a second end (a terminal end) disposed on the second slat 31b adjacent to the third slat 31c. In order to allow the second directionally inclined sectored plate 52a to connect the third slat 31c with the adjacent second slat 31b in an oblique manner, in a part provided with the sectored plate 52a, a reinforcement unit (sectored plate 52a) is provided between the third slat 31c and the adjacent second slat 31b throughout the entire axial length. The second directionally inclined sectored plate 52a inclines in a direction different from the first directionally inclined sectored plate 51a, specifically, in the opposite direction. In this embodiment, the first directionally inclined sectored plate 51a and the second directionally inclined sectored plate 52a are connected at a terminal end 54a.

In addition, the plunger inclination-prevention unit 5a of this embodiment includes a second axially inclined sectored plate (second directionally inclined sectored plate) 72 that is disposed below the second directionally inclined sectored plate 52a, having the first end (an initial end) disposed on an outer edge of the third slat 31c below the disk 34 by a predetermined length, extending obliquely downward with respect to the central axis 35 of the shaft 30 by a predetermined length, and having a second end (a terminal end) disposed on the second slat 31b adjacent to the third slat 31c. In this embodiment, a plurality of second directionally inclined sectored plates 72 is provided in the axial direction. The second axially inclined sectored plate 52a and the second axially inclined sectored plates 72 are substantially parallel to each other, and they are separated from each other by a substantially equidistance. In this embodiment, the first directionally inclined sectored plates 71 and the second directionally inclined sectored plates 72 are connected at a terminal end.

Similarly, between the third slat 31c and the second slat 31b and between the first slat 31a and the fourth slat 31d opposing each other across the central axis 35 of the shaft 30, there are provided the second directionally inclined sectored plate 52a and the plurality of second axially inclined sectored plates (second directionally inclined sectored plates, or second directionally inclined sectored plates with an initial end-on-slat) 72.

Figure 16:
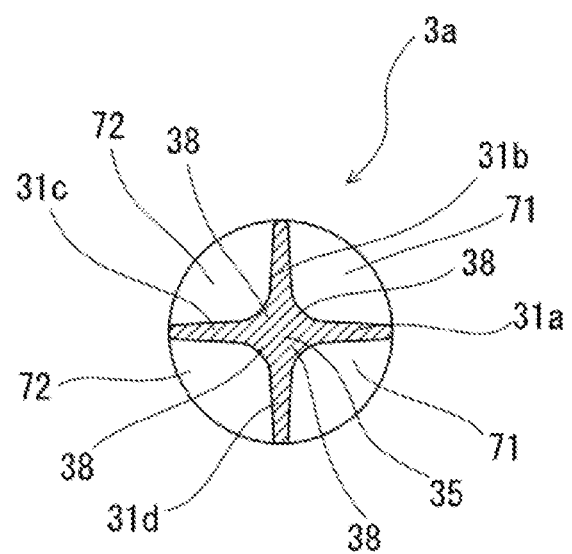
FIG. 16 is an enlarged cross-sectional view taken along line E-E of FIG. 13.
Figure 17:
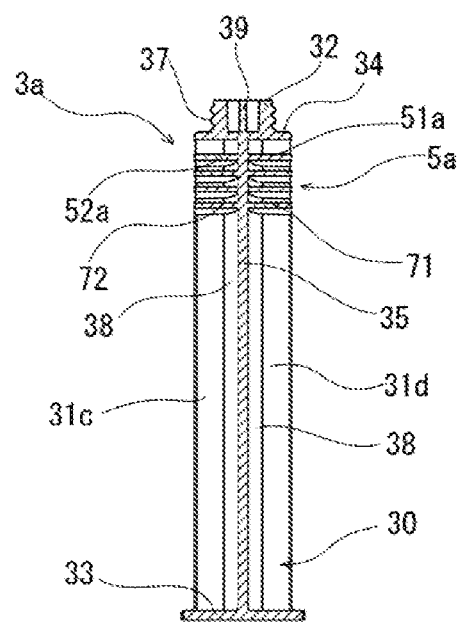
FIG. 17 is a cross-sectional view taken along line F-F of FIG. 15.
Figure 18:
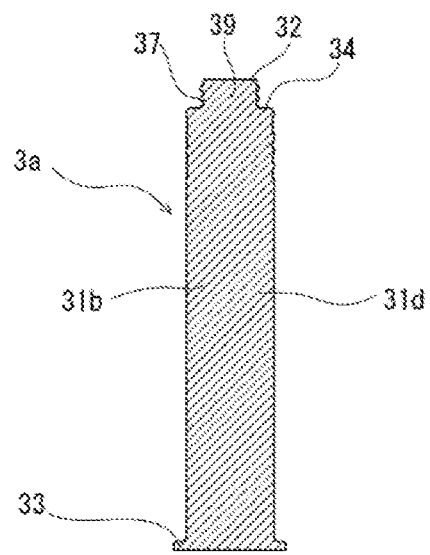
FIG. 18 is a cross-sectional view taken along line G-G of FIG. 15.

Even in such a plunger 3a of this embodiment, the axially inclined sectored plate is disposed between all the adjacent slats 31a, 31b, 31c, and 31d. Furthermore, as illustrated in FIGS. 16 and 17, outer edges of the axially inclined sectored plates 51a, 52a, 71, and 72 are positioned on the vertical line of the outer edge of the disk 34 or about the inner side of the vertical line. Particularly, in the plunger 3a of this embodiment, the outer edges of the axially inclined sectored plates are positioned substantially on the vertical line of the outer edge of the disk 34. Imagine a cylindrical body extending downward with an inner diameter equivalent to the outer periphery of the disk 34. The outer edges of the sectored plates 51a, 52a, 71, and 72 are positioned on an inner surface of the imaginary cylindrical body. In other words, the outer edges of the sectored plates 51a, 52a, 71, and 72 do not protrude from the inner surface of the imaginary cylindrical body.

Furthermore, in the plunger 3a of this embodiment, as illustrated in FIGS. 14 to 20, the plunger inclination-prevention unit 5a includes an arcuate plate 53a having a first end disposed on the disk 34 and extending downward along the shaft 30 with a predetermined width. The arcuate plate 53a is formed in pairs so as to face each other across the central axis of the plunger.

Specifically, the arcuate plate 53a has a first end disposed on the disk 34 and extends downward along the outer edge of the first slat 31a and the third slat 31c with a predetermined width. The initial end of the first directionally inclined sectored plate 51a is connected to the initial end of second directionally inclined sectored plate 52a in the arcuate plate 53a. Similarly, the initial end of each first directionally inclined sectored plate 71 is connected to the initial end of each second directionally inclined sectored plate 72 in the arcuate plate 53a. The arcuate plate 53a has a recess 61 provided in a connection of those plates.

The plunger inclination-prevention unit 5 of the plunger for a syringe may be configured as a plunger inclination-prevention unit 5b provided in a plunger 3b for a syringe illustrated in FIGS. 21 to 28. A difference between the plunger 3b for a syringe of this embodiment and the plunger 3 for a syringe of the aforementioned embodiment is only the configuration of the plunger inclination-prevention unit.

Figure 27:
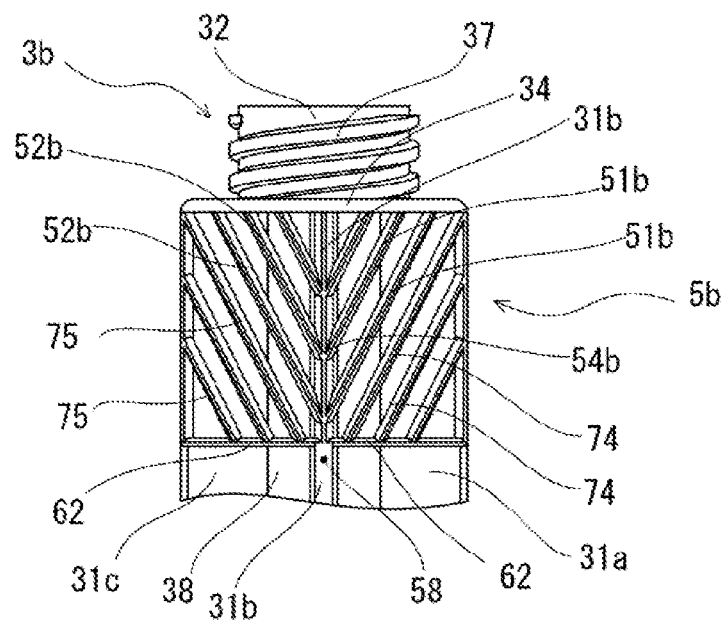
FIG. 27 is an enlarged view (enlarged front view) of a leading end of the plunger for a syringe illustrated in FIG. 21.
Figure 28:
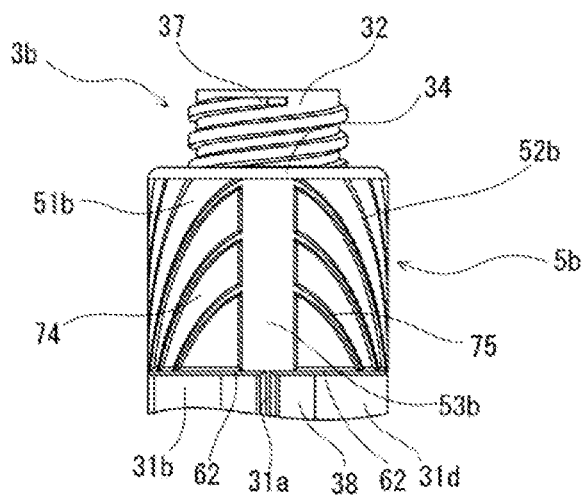
FIG. 28 is an enlarged view (enlarged right side view) of the leading end of the plunger for a syringe illustrated in FIG. 22.

In the plunger 3b of this embodiment, as illustrated in FIGS. 21 to 28, especially, in FIGS. 27 and 28, the plunger inclination-prevention unit 5b includes an axially inclined sectored plate (first directionally inclined sectored plate, or first directionally inclined sectored plate with an initial end-on-disk) 51b that is disposed between the first slat 31a and the second slat 31b, having a first end disposed on the disk 34, extending obliquely downward with respect to the central axis 35 of the shaft 30 by a predetermined length, and having a second end disposed on the second slat 31b. The plunger inclination-prevention unit 5b of this embodiment has a second disk 62 formed below the disk 34 by a predetermined length. Furthermore, the plunger inclination-prevention unit 5b of this embodiment includes an axially inclined sectored plate (first directionally inclined sectored plate with a terminal end-on-second disk) 74 that has a first end disposed on an intersection between the disk 34 and the first slat 31a the lower surface of the disk 34 and the upper end of the first slat 31a), extending obliquely downward with respect to the central axis 35 of the shaft 30 and toward the adjacent slat 31*b* by a predetermined length, and having a second end disposed on the second disk 62.

In the plunger inclination-prevention unit 5*b* of this embodiment, a plurality of, specifically, three, first directionally inclined sectored plates with the initial end-on-disk 51*b* are provided substantially parallel to each other at substantially regular intervals. Furthermore, in the plunger inclination-prevention unit 5*b* of this embodiment, a plurality of, specifically, three, first directionally inclined sectored plates with the terminal end-on-second disk 74 are also provided substantially parallel to each other at substantially regular intervals.

Furthermore, the plunger inclination-prevention unit 5*b* of this embodiment includes an axially inclined sectored plate (second directionally inclined sectored plate, or second directionally inclined sectored plate with an initial end-on-disk) 52*b* that is disposed between the third slat 31*c* and the second slat 31*b*, having a first end disposed on the disk 34, extending obliquely downward with respect to the central axis 35 of the shaft 30 by a predetermined length, and having a second end disposed on the second slat 31*b*. The plunger inclination-prevention unit 5*b* of this embodiment includes an axially inclined sectored plate (second directionally inclined sectored plate with a terminal end-on-second disk) 75 that has a first end disposed on an intersection between the disk 34 and the third slat 31*c* (the lower surface of the disk 34 and the upper end of the third slat 31*c*), extending obliquely downward with respect to the central axis 35 of the shaft 30 and toward the adjacent second slat 31*b* by a predetermined length, and having a second end disposed on the second disk 62.

In the plunger inclination-prevention unit 5*b* of this embodiment, a plurality of, specifically, three, second directionally inclined sectored plates with the initial end-on-disk 52*b* are provided substantially parallel to each other at substantially regular intervals. Furthermore, in the plunger inclination-prevention unit 5*b* of this embodiment, a plurality of, specifically, three, second directionally inclined sectored plates with the terminal end-on-second disk 75 are also provided substantially parallel to each other at substantially regular intervals. The second directionally inclined sectored plates 52*b* and 75 incline in a direction different from the first directionally inclined sectored plates 51*b* and 74. The first directionally inclined sectored plate 51*b* and the second directionally inclined sectored plate 52*b* are connected at a terminal end 54*b*. The terminal end 54*b* is positioned on each slat.

Similarly, between the first slat 31*a* and the second slat 31*b* and between the third slat 31*c* and the fourth slat 31*d* opposing each other across the central axis 35 of the shaft 30, there are provided the first directionally inclined sectored plate 51*b* and the plurality of first directionally inclined sectored plates with the terminal end-on-second disk 74.

Furthermore, similarly, between the third slat 31*c* and the second slat 31*b* and between the first slat 31*a* and the fourth slat 31*d* opposing each other across the central axis 35 of the shaft 30, there are provided the second directionally inclined sectored plate 52*b* and the plurality of second directionally inclined sectored plates with the terminal end-on-second disk 75.

In addition, in the plunger 3*b* of this embodiment, as illustrated in FIG. 28, the plunger inclination-prevention unit 5*b* includes an arcuate plate 53*b* having a first end disposed on the disk 34 and extending downward along the shaft 30 with a predetermined width. The arcuate plate 53*b* is formed in pairs so as to face each other across the central axis of the plunger. The initial end of each first directionally inclined sectored plate with the terminal-on-second disk 74 is connected to the initial end of each second directionally inclined sectored plate with the terminal end-on-second disk 75 in the arcuate plate 53*b*.

Furthermore, the terminal end of the first directionally inclined sectored plate 51*b* is connected to the terminal end of the second directionally inclined sectored plate 52*b*. In particular, as illustrated in FIG. 27, the terminal ends of the first directionally inclined sectored plate 51*b* and the second directionally inclined sectored plate 51*b* are connected at the outer edges of the second slat 31*b* and the fourth slat 31*d*.

In the plunger 3*b* of this embodiment, as illustrated in FIGS. 27 and 28, the second disk 62 has a diameter substantially equal to that of the disk 34. However, the second disk may have a diameter smaller than that of the disk 34 as a third disk 63 of a plunger 3*c* for a syringe of an embodiment illustrated in FIGS. 29 and 30.

Figure 29:
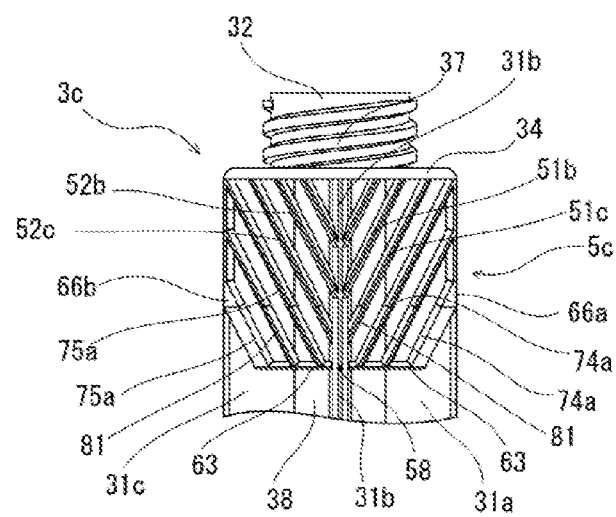
FIG. 29 is an enlarged front view of a leading end of a plunger for a syringe according to another embodiment.
Figure 30:
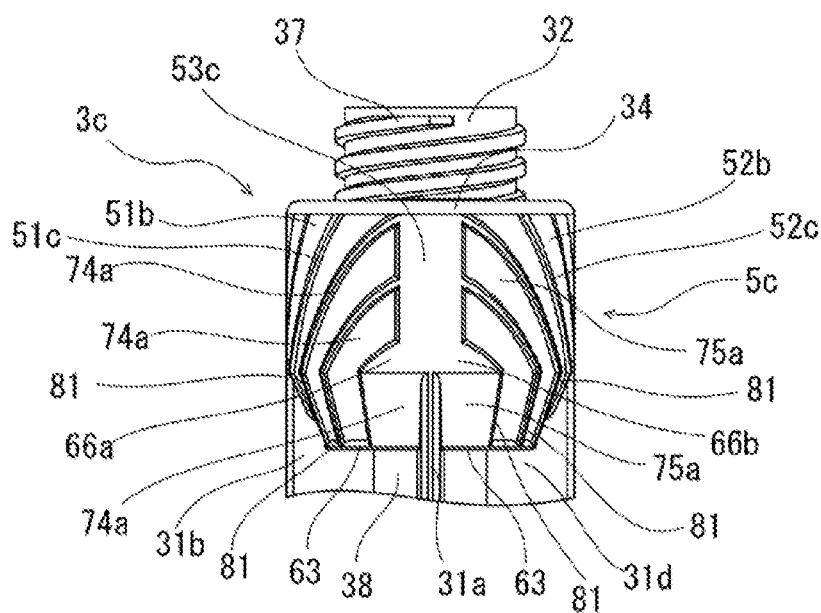
FIG. 30 is a right-side view of the leading end of the plunger for a syringe illustrated in FIG. 29.

Similar to the plunger 3*b* for a syringe of the aforementioned embodiment, in the plunger 3*c* of this embodiment, as illustrated in FIGS. 29 and 30, a plunger inclination-prevention unit 5*c* includes an axially inclined sectored plate (first directionally inclined sectored plate, or first directionally inclined sectored plate with an initial end-on-disk) 51*b* that is disposed between the first slat 31*a* and the second slat 31*b*, having a first end disposed on the disk 34, extending obliquely downward with respect to the central axis 35 of the shaft 30 by a predetermined length, and having a second end disposed on the second slat 31*b*. In this embodiment, two first directionally inclined sectored plates with the initial end-on-disk 51*b* are provided substantially in parallel to each other.

Furthermore, the plunger 3*c* for a syringe includes an axially inclined sectored plate (first directionally inclined sectored plate, or first directionally inclined sectored plate with an initial end-on-disk slat connection) 51*c* that is disposed below the inclined sectored plate 51*b*, having a first end disposed on the bottom surface of the disk 34, extending obliquely downward with respect to the central axis 35 of the shaft 30 by a predetermined length, and having a second end disposed on the second slat 31*b*. As illustrated in FIG. 30, the inclined sectored plate 51*c* has a lower end 81 that is inclined toward the center of the shaft 30.

In addition, the plunger inclination-prevention unit 5*c* includes an axially inclined sectored plate (first directionally inclined sectored plate with a terminal end-on-second disk) 74*a* that is disposed below the inclined sectored plate 51*c*, having a first end disposed on an upper end of the slat 31*a* (and the lower surface of the disk 34), extending obliquely downward with respect to the central axis 35 of the shaft 30 and toward the adjacent slat 31*b* by a predetermined length, and having a second end disposed on the second disk 63. In this embodiment, three first directionally inclined sectored plates with a terminal end-on-second disk 74*a* are provided substantially in parallel to each other. As illustrated in FIG. 30, the inclined sectored plate 74*a* has a lower end 81 that is inclined toward the center of the shaft 30.

Furthermore, in the plunger 3*c* for a syringe of this embodiment, the plunger inclination-prevention unit 5*c* includes an axially inclined sectored plate (second directionally inclined sectored plate, or second directionally inclined sectored plate with an initial end-on-disk) 52*b* that is disposed between the third slat 31*c* and the second slat 31*b*, having a first end disposed on the disk 34, extending obliquely downward with respect to the central axis 35 of the shaft 30 by a predetermined length, and having a second end disposed on the second slat 31*b*. In this embodiment, two second directionally inclined sectored plates with the initial end-on-disk 52b are provided substantially in parallel to each other.

Still further, the plunger 3c for a syringe includes an axially inclined sectored plate (second directionally inclined sectored plate, or second directionally inclined sectored plate with an initial end-on-disk slat connection) 52c that is disposed below the inclined sectored plate 52b, having a first end disposed on the lower surface of the disk 34, extending obliquely downward with respect to the central axis 35 of the shaft 30 by a predetermined length, and having a second end disposed on the second slat 31b. As illustrated in FIG. 30, the inclined sectored plate 52c has a lower end 81 that is inclined toward the center of the shaft 30.

Still further, the plunger inclination-prevention unit 5c includes an axially inclined sectored plate (second directionally inclined sectored plate with a terminal end-on-second disk) 75a that is disposed below the inclined sectored plate 52c, having a first end disposed on the upper end of the slat 31c (and the lower surface of the disk 34), extending obliquely downward with respect to the central axis 35 of the shaft 30 and toward the adjacent slat 31b by a predetermined length, and having a second end disposed on the second disk 63. In this embodiment, three second directionally inclined sectored plates with the terminal end-on-second disk 75a are provided substantially in parallel to each other. As illustrated in FIG. 30, the inclined sectored plate 75a has a lower end 81 that is inclined toward the center of the shaft 30.

Similarly, between the first slat 31a and the second slat 31b and between the third slat 31c and the fourth slat 31d opposing each other across the central axis 35 of the shaft 30, there are provided the first directionally inclined sectored plates 51b, 51c and 74a. Similarly, between the third slat 31c and the second slat 31b and between the first slat 31a and the fourth slat 31d opposing each other across the central axis 35 of the shaft 30, there are provided the second directionally inclined sectored plates 52b, 52c and 75a.

In addition, in the plunger 3c of this embodiment, as illustrated in FIG. 30, the plunger inclination-prevention unit 5c includes an arcuate plate 53c having a first end disposed on the disk 34 and extending downward along the shaft 30 with a predetermined width. The arcuate plate 53c is formed in pairs so as to face each other across the central axis of the plunger. The initial end of the first directionally inclined sectored plate with the terminal-on-second disk 74a is connected to the initial end of second directionally inclined sectored plate with the terminal end-on-second disk 75a in the arcuate plate 53c.

In addition, in the plunger 3c of this embodiment, the first directionally inclined sectored plate 74a placed at the lowest position is connected to the lower end of the arcuate plate 53c, and an extending portion 66a that extends in a circumferential direction is provided in the lower end of the arcuate plate 53c. Similarly, the second directionally inclined sectored plate 75a placed at the lowest position is also connected to the lower end of the arcuate plate 53c, and an extending portion 66b that extends in the opposite direction of the extending portion 66a in the circumferential direction is provided in the lower end of the arcuate plate 53c.

A plunger for a syringe according to one embodiment of has the follow features:

(1) A plunger for a syringe,
the plunger including: a gasket mounting portion provided at an upper end of the plunger; a disk positioned at a lower end of the gasket mounting portion; a shaft extending downward from the disk; and a pressing portion provided at a lower end portion of the shaft, wherein the shaft includes a plurality of slats extending downward from the disk, and the plunger includes a plunger inclination-prevention unit that is provided at a leading end of the shaft and is configured to prevent the plunger from inclining inside a barrel, and the plunger inclination-prevention unit includes an axially inclined plate that has a first end disposed on the disk, extending obliquely downward with respect to a central axis of the shaft, and having a second end disposed on any one of the slats, and the axially inclined plate has an outer edge positioned on a vertical line of an outer edge of the disk or about the vertical line, the axially inclined plate being provided between all the adjacent slats.

Particularly, the outer edge of the axially inclined plate is positioned on the vertical line of the outer edge of the disk or about the inner side of the vertical line, and the axially inclined plate is provided between all the adjacent slats. Therefore, the plunger inclination-prevention unit substantially does not include a portion with no axially inclined plate, so that it is possible to prevent inclination of the plunger in its entirety. Accordingly, the plunger does not incline inside the barrel after being mounted on the gasket of the syringe, which causes no liquid leakage due to the inclination of the plunger. In addition, even during the mounting operation of the plunger on the gasket, the plunger does not inline inside the barrel, so that the mounting operation can be performed satisfactorily.

In addition, the aforementioned embodiment may have the follow features.

(2) The plunger for a syringe according to (1), wherein the axially inclined plate has a first end at an intersection between the disk and the slat and a second end between the slat adjacent to the slat.

(3) The plunger for a syringe according to (1) or (2), wherein the axially inclined plate is provided in plural between the adjacent slats.

(4) The plunger for a syringe according to any one of (1) to (3), wherein the plurality of the axially inclined plates provided between the adjacent slats intersects with each other.

(5) The plunger for a syringe according to any one of (1) to (3), wherein the plurality of the axially inclined plates provided between the adjacent slats is substantially in parallel with each other.

(6) The plunger for a syringe according to any one of (1) to (5), wherein the plunger inclination-prevention unit includes an axially inclined plate that has a first end disposed on the slat, extending obliquely downward with respect to the central axis of the shaft, and having a second end disposed on the slat adjacent to the slat.

(7) The plunger for a syringe according to any one of (1) to (6), wherein the plunger inclination-prevention unit includes a second disk formed below the disk; and an axially inclined plate that has a first end disposed on an upper end of the slat, extending obliquely downward with respect to the central axis of the shaft, and having a second end disposed on the second disk.

(8) The plunger for a syringe according to any one of (1) to (6), wherein the plunger inclination-prevention unit includes an arcuate plate having a first end disposed on the disk, extending downward along the shaft with a predetermined width.

(9) The plunger for a syringe according to any one of (1) to (8), wherein the shaft has four slats extending downward from the disk.

A pre-filled syringe according to one embodiment has the follow feature.

(10) A pre-filled syringe including a plunger for a syringe and a drug pre-filled barrel, wherein the plunger for a syringe is the plunger for a syringe according to any one of (1) to (9), and the drug pre-filled barrel includes a sealed leading end; a barrel main body including a flange provided at a base end of the barrel main body; a gasket that is stored inside the base end of the barrel main body and on which the plunger for a syringe is mountable; and a drug stored inside the barrel main body.

In addition, the aforementioned embodiment may have the follow feature.

(11) The pre-filled syringe according to (10), wherein the plunger for a syringe is not mounted on the drug pre-filled barrel, and the plunger for a syringe is to be mounted on the drug pre-filled barrel when used.

What is claimed is:

1. A plunger for a syringe that comprises a barrel, the plunger comprising:
    a gasket mounting portion located at a distal end of the plunger;
    a disk positioned at a proximal end of the gasket mounting portion;
    a shaft extending proximally from the disk, wherein the shaft comprises three or more slats extending proximally from the disk, wherein the three or more slats include a first slat, a second slat that is adjacent to the first slat, and a third slat that is adjacent to the second slat;
    a pressing portion located at a proximal end of the shaft; and
    a plunger inclination-prevention unit that is located at a distal end of the shaft and is configured to inhibit the plunger from inclining inside the barrel of the syringe, wherein the plunger inclination-prevention unit comprises a plurality of axially inclined plates, wherein each of the plurality of axially inclined plates has an outer edge positioned at or proximate to an outer edge of the disk, and wherein the plurality of axially inclined plates includes:
        a first axially inclined plate that has a first end disposed on the disk, extends obliquely proximal with respect to a central axis of the shaft, and has a second end disposed on the second slat, and
        a second axially inclined plate that has a first end disposed on the disk, extends obliquely proximal with respect to the central axis of the shaft, and has a second end disposed on the first slat,
        wherein the first axially inclined plate intersects the second axially inclined plate.

2. The plunger for a syringe according to claim 1, wherein:
    the first end of the first axially inclined plate is located at an intersection between the disk and the first slat; and
    the first end of the second axially inclined plate is located at an intersection between the disk and the second slat.

3. The plunger for a syringe according to claim 1, wherein:
    the plurality of axially inclined plates includes:
        a third axially inclined plate that has a first end disposed on the disk, extends obliquely proximal with respect to a central axis of the shaft, and has a second end disposed on the second slat, and
        a fourth axially inclined plate that has a first end disposed on the disk, extends obliquely proximal with respect to the central axis of the shaft, and has a second end disposed on the third slat,
    wherein the third axially inclined plate intersects the fourth axially inclined plate.

4. The plunger for a syringe according to claim 3, wherein:
    the first end of the third axially inclined plate is located at an intersection between the disk and the third slat; and
    the first end of the fourth axially inclined plate is located at an intersection between the disk and the second slat.

5. The plunger for a syringe according to claim 1, wherein the first and second axially inclined plates are arcuate plates.

6. The plunger for a syringe according to claim 1, wherein the three or more slats include a fourth slat that is adjacent to the first slat and the third slat.

7. A pre-filled syringe comprising:
    the plunger according to claim 1; and
    the barrel recited in the preamble of claim 1, wherein the barrel is filled with a drug;
    wherein the barrel comprises:
        a sealed distal end,
        a barrel main body comprising a flange located at a proximal end of the barrel main body, and
        a gasket located inside a proximal end portion of the barrel main body, and on which the plunger for a syringe is mountable.

8. A kit comprising:
    the plunger according to claim 1; and
    the barrel recited in the preamble of claim 1, wherein the barrel is filled with a drug;
    wherein the barrel comprises:
        a sealed distal end,
        a barrel main body comprising a flange located at a proximal end of the barrel main body, and
        a gasket located inside a proximal end portion of the barrel main body, and on which the plunger for a syringe is mountable
    wherein the plunger is not mounted on the drug filled barrel, and the plunger is configured to be mounted on the drug filled barrel when used.

* * * * *